(12) United States Patent
Gidon et al.

(10) Patent No.: US 8,994,949 B2
(45) Date of Patent: Mar. 31, 2015

(54) OPTICAL GAS DETECTOR

(71) Applicant: Commissariat à l'énergie atomique et aux énergies alternatives, Paris (FR)

(72) Inventors: Serge Gidon, La Murette (FR); Pierre Gidon, Echirolles (FR)

(73) Assignee: Commissariat a l'energie atomique et aux energies alternatives, Paris (FR)

( * ) Notice: Subject to any disclaimer, the term of this patent is extended or adjusted under 35 U.S.C. 154(b) by 27 days.

(21) Appl. No.: 14/032,004

(22) Filed: Sep. 19, 2013

(65) Prior Publication Data

US 2014/0078494 A1    Mar. 20, 2014

(51) Int. Cl.
*G01N 21/00*      (2006.01)
*G01N 21/61*      (2006.01)
*G01N 21/31*      (2006.01)
*G01N 21/359*     (2014.01)

(52) U.S. Cl.
CPC .............. *G01N 21/61* (2013.01); *G01N 21/314* (2013.01); *G01N 21/359* (2013.01)
USPC ............................ 356/437; 356/236; 250/228

(58) Field of Classification Search
USPC ........................... 356/432–440, 236; 250/228
See application file for complete search history.

(56) References Cited

U.S. PATENT DOCUMENTS

| | | | |
|---|---|---|---|
| 4,088,407 A | 5/1978 | Schoeffel et al. | |
| 4,657,397 A * | 4/1987 | Oehler et al. | 356/414 |
| 4,988,205 A * | 1/1991 | Snail | 356/446 |
| 5,309,339 A * | 5/1994 | Webb | 362/259 |
| 5,401,966 A | 3/1995 | Gray et al. | |
| 5,745,234 A * | 4/1998 | Snail et al. | 356/236 |
| 7,119,337 B1 | 10/2006 | Johnson et al. | |
| 8,625,088 B2 * | 1/2014 | Park et al. | 356/236 |
| 2008/0204884 A1 * | 8/2008 | Jang | 359/599 |
| 2013/0050704 A1 * | 2/2013 | Padilla Viquez | 356/402 |
| 2014/0078504 A1 * | 3/2014 | Nicoletti et al. | 356/437 |
| 2014/0354989 A1 * | 12/2014 | Marbach et al. | 356/301 |

FOREIGN PATENT DOCUMENTS

DE    102010008091 A1    9/2011

OTHER PUBLICATIONS

Institut National de la Propriete Industrielle, Preliminary Search Report, dated Jun. 20, 2013 for FR12/58833.

* cited by examiner

*Primary Examiner* — Hoa Pham
(74) *Attorney, Agent, or Firm* — Kevin R. Erdman; Brannon Sowers & Cracraft PC

(57) ABSTRACT

A gas detector including an assembly of two hemispherical caps having opposite concavities, and which are reflective on at least a portion of their opposite surfaces, and a wafer arranged in an equatorial plane of the assembly of the two caps, in the vicinity of but spaced apart from the center of the equatorial plane, including, back-to-back: a diverging light emitter directed towards the first cap and a light receiver directed towards the second cap.

12 Claims, 2 Drawing Sheets

OPTICAL GAS DETECTOR

CROSS-REFERENCE TO RELATED APPLICATION

The present application claims priority under 35 U.S.C. §119 of French Patent Provisional Application Serial Number 12/58,833, filed Sep. 20, 2012, the disclosures of which are incorporated by reference herein.

BACKGROUND

The present disclosure relates to an optical detector of the presence, and possibly of the content, of a gas in an atmosphere.

STATE OF THE ART

The use of optical detectors of the presence of a gas, for example, carbon dioxide $CO_2$, carbon monoxide CO, methane, or possibly various toxic gases such as xylene or toluene released by paints, is known. It should be noted that a detector of the presence of an excess of $CO_2$ may form a fire detector.

Optical detectors which detect the presence of a gas by measuring the absorption of a light beam at one or several wavelengths corresponding to one or several absorption lines of the considered gas will here be considered. In such detectors, an optical beam is emitted by a light source emitting in a wavelength range comprising the wavelength(s) of absorption lines characteristic of the gas to be detected. A receiver preceded by a filter at the wavelength of the absorption line to be detected indicates the absorption at this wavelength, and the presence and the content of the considered gas can be deduced therefrom. For such detectors to operate satisfactorily, two receivers or two receive areas are generally provided, the second receiver being intended to provide a reference indication at wavelengths other than the wavelength of the absorption line. This reference is especially used to take into account environmental fluctuations (for example, the air moisture), intensity fluctuations in the emission source and/or the sensitivity of the detection chain.

So that the entire gas detection system can have a small bulk, it is often provided for the light beam propagating between the emitter and the receiver to travel one or several times back and forth via reflector systems. It is for example provided for laser beams to undergo multiple reflections in a resonant cavity where the gas to be detected is likely to be present.

Generally, existing gas detection systems implying at least one back and forth travel of light beams between the emitter and the receiver have the disadvantage of being relatively delicate to manufacture. Indeed, they require an accurate positioning of the emitter and of the receiver with respect to the reflector systems determining the optical path between the emitter and the receiver.

Thus, there is a need for an optical absorption gas detector which is particularly simple to manufacture and which is tolerant to misalignments between the emitter, the reflective surfaces, and the receiver.

SUMMARY

An embodiment provides a device overcoming at least some of the disadvantages of existing devices.

Thus, an embodiment provides a gas detector, comprising: an assembly of two hemispherical caps having opposite concavities, and which are reflective on at least a portion of their opposite surfaces, and a wafer arranged in an equatorial plane of the assembly of the two caps, in the vicinity of but spaced apart from the center of the equatorial plane, comprising, back-to-back: a diverging light emitter directed towards the first cap and a light receiver directed towards the second cap.

According to an embodiment, the two hemispherical caps are assembled in a sphere.

According to an embodiment, the two hemispherical caps are spaced apart from each other by a ring.

According to an embodiment, the light receiver comprises at least two portions detecting different wavelengths.

According to an embodiment, the wafer is supported by a tab bearing on at least one edge of the caps, the tab being located in the equatorial plane of the caps.

According to an embodiment, the tab is made of a material transparent to the wavelengths that the gas detector aims at detecting.

According to an embodiment, the light emitter and receiver are formed in plate portions having their rear surfaces placed against each other.

According to an embodiment, the reflective portion of the two hemispherical caps is located at a latitude greater 60° with respect to the equatorial plane.

According to an embodiment, the emitter-receiver assembly is placed at a distance from the center of the equatorial plane ranging between 5 and 10% of the radius of the hemispherical caps.

An embodiment further provides an imager detector, comprising a gas detector such as described hereabove, an imager being further formed on the tab.

According to an embodiment, the imager is an infrared imager.

According to an embodiment, the imager detector comprises a support with several support arms clamping the hemispherical caps and directing them.

According to an embodiment, a gas detector comprises an assembly of two hemispherical caps having opposite concavities, and which are reflective on at least a portion of their opposite surfaces, and a plate arranged in an equatorial plane of the assembly of the two caps, in the vicinity of but spaced apart from the center of the equatorial plane, comprising, back-to-hack: a diverging light generator directed towards the first cap, and a light detector directed towards the second cap. The detector may have two hemispherical caps that are assembled in a sphere. The detector may have the two hemispherical caps that are spaced apart from each other by a ring. The detector may have the light detector comprising at least two portions detecting different wavelengths. The detector may have the wafer supported by a tab bearing on at least one edge of said caps, said tab being located in said equatorial plane of the caps. The detector may have the tab made of a material transparent to the wavelengths that the gas detector aims at detecting. The detector may have the light generator and detector formed in plate portions having their rear surfaces placed against each other. The detector may have the reflective portion of the two hemispherical caps located at a latitude greater 60° with respect to said equatorial plane. The detector may have the generator-detector assembly placed at a distance from the center of the equatorial plane ranging between 5 and 10% of the radius of the hemispherical caps.

An imager detector, may comprise comprising the gas detector above, with an imager being further formed on said tab. The imager detector may have the imager as an infrared imager. The imager detector may further comprise several support arms clamping the hemispherical caps and directing said caps.

The foregoing and other features and advantages will be discussed in detail in the following non-limiting description of specific embodiments in connection with the accompanying drawings.

BRIEF DESCRIPTION OF THE DRAWINGS

The foregoing and other features and advantages will be discussed in detail in the following non-limiting description of specific embodiments in connection with the accompanying drawings, among which.

Figure 1:
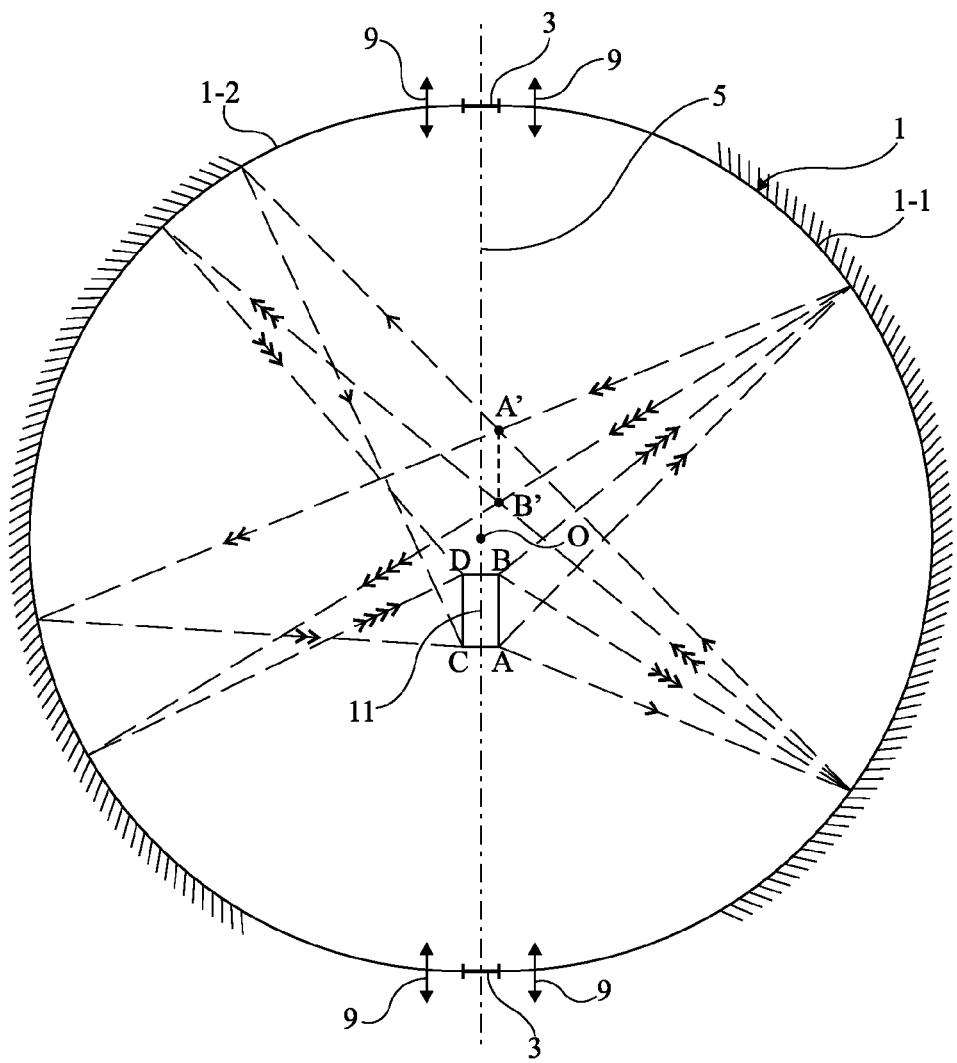
FIG. 1 is a cross-section view of an embodiment of an optical gas detector tolerant to misalignments.

Corresponding reference characters indicate corresponding parts throughout the several views. Although the drawings represent embodiments of the present invention, the drawings are not necessarily to scale and certain features may be exaggerated in order to better illustrate and explain the present invention. The exemplification set out herein illustrates an embodiment of the invention, in one form, and such exemplifications are not to be construed as limiting the scope of the invention in any manner.

DETAILED DESCRIPTION

The embodiments disclosed below are not intended to be exhaustive or limit the invention to the precise form disclosed in the following detailed description. Rather, the embodiments are chosen and described so that others skilled in the art may utilize their teachings.

FIG. 1 is a cross-section view showing an embodiment of an absorption gas detector.

The detector comprises a hollow spherical structure 1, for example, having a size ranging between the size of a ping-pong ball and the size of a tennis ball (diameter preferably smaller than 10 cm). The internal walls of this sphere are reflective for a wavelength of interest or a wavelength range of interest. Although a spherical structure has been mentioned hereabove and will be described hereafter, it should be noted that the structure may be approximately spherical. For example, as shown in FIG. 1, two hemispherical caps 1-1, 1-2 may be assembled with opposite concavities via a ring 3 maintaining a slight spacing between the two hemispherical caps. Ring 3 is not necessarily a hardware element separate from each of the two hemispherical caps but may simply be means of assembly of these two hemispherical caps, such as generally used in ping-pong ball manufacturing.

An emitter-receiver assembly or plate 11 is arranged on an equatorial plane 5 inside of the sphere (real equatorial plane in the case of a spherical structure, plane orthogonal to the middle of ring 3 in the case where the two caps are spaced apart by a ring 3). Emitter-receiver assembly or plate 11 is shown in the form of a small wafer having an emitting surface AB facing one of hemispherical caps 1-1 and a receiving surface CD facing opposite hemispherical cap 1-2.

The emitter-receiver is arranged in the equatorial plane and is offset in this plane from center O of the sphere. The emitter preferably is a non-directional or little directional emitter (diverging emitter) such as a heated filament. It can be seen by the drawing of extreme rays indicated in FIG. 1 that hemispherical cap 1-1 provides a symmetrical image of surface AB of the emitter in equatorial plane A'B' and that hemispherical cap 1-2 sends back image A'B' on receiving surface CD of emitter-receiver 11.

Simulations performed by the inventors show that such a system is practically insensitive to misadjustments within certain intervals. Indeed, if emitter-receiver assembly or plate 11 is offset in the equatorial plane by a value ranging from 5 to 10% of radius R of the hemispherical caps, the light intensity received by receiving side CD of device or plate 11 varies by less than 10%. Similarly, if emitter-receiver system or plate 11 is offset orthogonally to the equatorial plane, by a value ranging from 5 to 10% of the radius of the hemispherical caps, this causes a variation of the received intensity also lower than 10%.

Such a large positioning tolerance is especially due to the fact that the emitting portion, on side AB, and the receiving portion, on side CD, of emitter-receiver assembly 11 are assembled head-to-tail in a single block, whereby the emitter and the receiver(s) move together and this simultaneous displacement compensates for the consequences of possible mispositionings.

Further, the sphere preferably comprises, on the side of the intersection between this sphere and equatorial plane 5, one or several openings 9 intended for the circulation of the ambient gas of the environment where the sphere is placed.

Figure 2A:
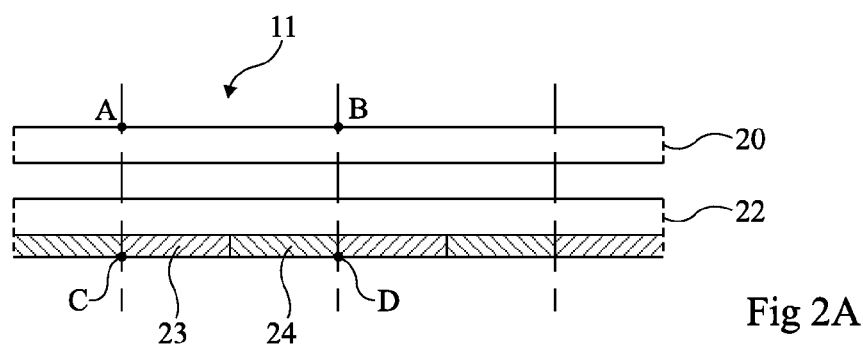
FIG. 2A is a cross-section view at an intermediate stage of the assembly of an embodiment of an emitter-receiver-filter assembly

FIG. 2A illustrates, as an example, a step of manufacturing an example of embodiment of an emitter-receiver assembly 11. Many emitters are formed on a first plate 20, for example, a silicon plate, possibly assembled on a plate of an insulating material such as silica or sapphire. The emitter will not be described in detail since its manufacturing technology is well known. It may be a platinum or titanium nitride filament formed on the plate by any known means. In operation, the filament is heated by the flowing of the electric current up to a temperature greater than 200° C. capable of providing a sufficient quantity of radiation in a wavelength range containing the absorption line to be detected, for example, at 650° C. for a central wavelength of 4.25 μm in the case where the gas to be detected is $CO_2$. Advantageously, such a temperature is compatible with a long lifetime of the filament.

The receivers on the CD side of device 11 are formed on a second plate 22 also by any known means. The second plate preferably is a silicon plate having passive components (resistors, capacitances, ferroelectric capacitances . . . ) or active components (diodes or transistors) integrated therein, having characteristics which are variable according to their heating on reception of infrared rays. In particular, the receivers may be bolometric receivers, for example formed of a membrane which absorbs infrared rays and heats up, the temperature rise of the membrane implying a variation of its detectable resistance.

Each receiver CD may be coated with at least one filter. Two filters 23, 24 are shown in the cross-section view of FIG. 2A, respectively centered on the absorption line to be detected and on a second wavelength. The second wavelength may enable to detect another gas, or even, for example, to process the reference path. The filters may correspond to stacks of thin dielectric layers. It may also be an alternation of metallic and insulating strips having a step and a spacing determining the filtering frequency.

Figure 2B:
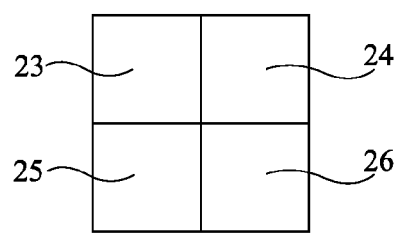
FIG. 2B is a partial top view of an embodiment of an element of the assembly of FIG. 2A.

Then, plates 20 and 22 are placed against each other so that surfaces AB and CD form opposite external surfaces, and are sawn into elementary wafers, each corresponding to an emitter-receiver assembly, according to the sawing lines illustrating in vertical dotted lines in FIG. 2A. Advantageously, complete systems comprising a source, one or several fillers, and one or several receivers, are collectively formed on a wafer, and then sawn into individual systems. Such a collective production of the complete systems provides a low manufacturing cost The bottom view of FIG. 2B shows a case where four filters 23, 24, 25, 26 intended, for example, to respectively receive a reference wavelength or wavelength range and three specific wavelengths, for example corresponding to three absorption lines of a same gas to be detected or to absorption lines of several gases to be detected, have been provided. Each filter is associated with a receiver, for example, of bolometric type. Wafer 11 for example has a side length ranging from 1 to 5 mm and thickness ranging from 1 to 2 mm.

Figure 2C:
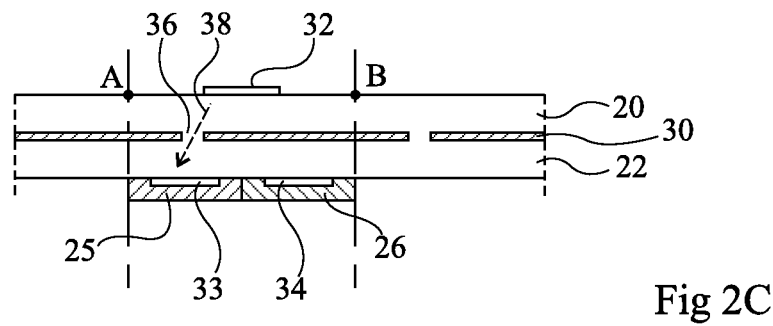
FIG. 2C is a cross-section view of an alternative embodiment of an emitter-receiver-filter assembly.

FIG. 2C is a cross-section view of an alternative embodiment of an emitter-receiver-filter assembly. In certain cases, plates 20, 22 are transparent to the concerned wavelengths. Such is for example the case for silicon plates at wavelengths close to 4.25 µm. In this case, a layer forming a bather against the transmission of direct radiations through the plates is placed between the emitter and the receiver(s). A layer 30 opaque to radiations, for example, a metal layer, formed on at least one of the two plates before assembly thereof, may for example be placed.

In the representation of FIG. 2C, a rectangle 32 symbolizes the emitter area on surface AB of the upper plate and rectangles 33, 34 are used to symbolize two receiver areas on surface CD of the lower plate, respectively covered with filters 25, 26. Opaque layer 30 comprises, in an alternative embodiment, an opening 36 for giving way to a direct radiation 38 from emitter 32 to receiver 33. In this variation, "filter" 25 covering receiver 33 is then opaque. Receiver 33 then provides a reference signal representative of the sole fluctuations of emitter 32.

Figure 3:
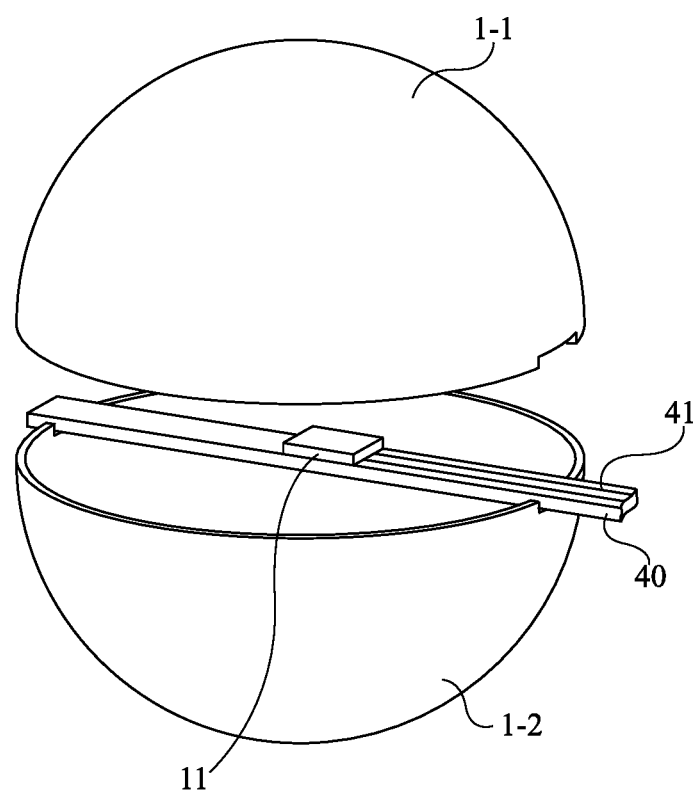
FIG. 3 is a perspective view of an embodiment of an absorption optical gas detector.

FIG. 3 is a perspective view representing an example of assembly of emitter-receiver block or plate 11 inside of a sphere having at least partly reflective inner walls. Wafer or plate 11 is assembled on a tab 40 having metal tracks 41 intended to provide the connections to the emitter and to the receiver(s) implanted therein. The tab may be made of a transparent material in the wavelength range to be detected, for example of silicon or sapphire, such materials being substantially transparent to a 4.25-flm wavelength. It may also be provided for the tab to comprise, opposite to the wafer, an opening intended to give way to light rays (image A'B' in FIG. 1).

In the shown non-limiting example, tab 40 bears at least on one of the edges of hemispherical caps 1-1, 1-2. A notch may be defined from this edge to help the alignment It should be understood that the present invention is likely to have many alterations, as concerns the number of optical emitters, the number of optical receivers and of associated filters, as well as the nature of these emitters and receivers and the forming of the head-to-tail assembly of an emitter and of receivers.

Further, as shown in FIG. 1 with lateral hatchings, only a portion of the inside of the sphere may also be made reflective. In practice, it is possible to provide a metallization of the walls of the hemispherical caps to make them reflective, or even a deposition of a stack of specific dielectric layers. The metallization may be performed on a section only of their surfaces, for example located at latitudes greater than 60° relative to the equatorial plane. This enables to limit the loss of rays which would be reflected under too strong an incidence.

Further, the metal deposition enabling to make the inner surfaces of the hemispherical caps reflective may be performed so that the reflective surface is slightly rough (and diffusing) to blur the image of the filament on the receiver in order to further increase the tolerance to manufacturing imperfections.

According to an alternative embodiment, other functions may be integrated in the sphere, in combination with or independently from the gas detector function.

It may especially be provided to integrate an imager on tab 40, for example in the form of an integrated circuit Such an imager may be an infrared imager, sensitive to wavelengths which are not stopped by the reflective material deposited on the walls of the hemispherical caps. Such an imager may be used to perform a detection of the position or of the motion of people in the room where the sphere is placed.

In this embodiment, the reflective material deposited on the walls of the hemispherical caps will be provided to be reflective at the gas detection wavelength, and to be transmissive at the imager observation wavelength. As an example, if the detected gas is $CO_2$ and the image is provided to acquire images in infrared, the material deposited on the lower surfaces of the hemispherical caps may be a silicon layer having an optical thickness on the order of 2.1 µm. Indeed, such a thickness is substantially equal to $\lambda_1/2$ for absorption wavelength $\lambda_1$ of $CO_2$, that is, it forms a reflective layer, and is equal to $\lambda_2/4$ for an infrared absorption wavelength $\lambda_2$ equal to 10 µm, that is, transmissive.

A system comprising a $CO_2$ detector having an absorption line at approximately 4.25 µm, and an infrared imager for wavelengths in the 8-12 µm band, which corresponds to the infrared emission of the human body, is thus defined.

As seen previously, the material deposited on the cap walls may be a stack of several layers, for example, of two silicon layers separated by a layer made of a material of low optical index, such as zinc sulfide (ZnS), silicon nitride SiN, or silicon oxide $SiO_2$.

The imager positioning will be provided to avoid disturbing the rays reflected in the ball for the gas detection. To achieve this, the imager may for example be placed on tab 40 outside of areas ABCD and A'B'C'D', or even outside of the cross-section plane of FIG. 1.

Further, the spherical (or quasi-spherical) shape of the gas detector provided herein is particularly well adapted to the integration of the imager in a room, the spherical structure being maintained by a mechanical device in a position which is for example fixed with respect to a wall or to a ceiling in a room. It should also be noted that the spherical shape may also be assembled in a support comprising several support aims clamping the ball, the aims being rigidly attached to a base which can be affixed in a room. A mechanical system may then be provided to direct the ball in a desired direction. This last case may be specifically advantageous if an imager is integrated in the ball enclosure.

Finally, advantageously, source-filter-receiver sys-tems may be formed collectively, which limits their manufacturing cost.

Such alterations, modifications, and improvements are intended to be part of this disclosure, and are intended to be within the spirit and the scope of the present invention. Accordingly, the foregoing description is by way of example only and is not intended to be limiting. The present invention is limited only as defined in the following claims and the equivalents thereto.

What is claimed is:

1. A gas detector comprising:
   an assembly of two hemispherical caps having opposite concavities, and which are reflective on at least a portion of their opposite surfaces, and
   a plate arranged in an equatorial plane of the assembly of the two caps, in the vicinity of but spaced apart from the center of the equatorial plane, comprising, back-to-back, a generator-detector assembly of:
      a diverging light generator directed towards the first cap, and
      a light detector directed towards the second cap.

2. The detector of claim 1, wherein the two hemispherical caps are assembled in a sphere.

3. The detector of claim 1, wherein the two hemispherical caps are spaced apart from each other by a ring.

4. The detector of claim 1, wherein the light detector comprises at least two portions detecting different wavelengths.

5. The detector of claim 1, wherein the plate is supported by a tab bearing on at least one edge of said caps, said tab being located in said equatorial plane of the caps.

6. The detector of claim 5, wherein the tab is made of a material transparent to the wavelengths that the gas detector aims at detecting.

7. The detector of claim 1, wherein the light generator and detector are formed in plate portions having their rear surfaces placed against each other.

8. The detector of claim 1, wherein the reflective portion of the two hemispherical caps is located at a latitude greater 60° with respect to said equatorial plane.

9. The detector of claim 1, wherein the generator-detector assembly is placed at a distance from the center of the equatorial plane ranging between 5 and 10% of the radius of the hemispherical caps.

10. An imager detector, comprising:
    a gas detector comprising:
       an assembly of two hemispherical caps having opposite concavities, and which are reflective on at least a portion of their opposite surfaces, and
       a plate arranged in an equatorial plane of the assembly of the two caps, in the vicinity of but spaced apart from the center of the equatorial plane, the plate being supported by a tab bearing on at least one edge of said caps, said tab being located in said equatorial plane of the caps, the plate comprising, back-to-back, a generator-detector assembly of:
          a diverging light generator directed towards the first cap, and
          a light detector directed towards the second cap; and
       an imager being further formed on said tab.

11. The imager detector of claim 10, wherein the imager is an infrared imager.

12. The imager detector of claim 10, further comprising several support arms clamping the hemispherical caps and directing said caps.

* * * * *